United States Patent
Benie et al.

(10) Patent No.: US 10,837,006 B2
(45) Date of Patent: Nov. 17, 2020

(54) POLYPEPTIDES HAVING PROTEASE ACTIVITY AND POLYNUCLEOTIDES ENCODING SAME

(71) Applicant: Novozymes A/S, Bagsvaerd (DK)

(72) Inventors: Astrid Benie, Vaerloese (DK); Morten Gjermansen, Greve (DK); Peter Rahbek Oestergaard, Virum (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/062,660

(22) PCT Filed: Jan. 20, 2017

(86) PCT No.: PCT/EP2017/051142
§ 371 (c)(1),
(2) Date: Jun. 15, 2018

(87) PCT Pub. No.: WO2017/125527
PCT Pub. Date: Jul. 27, 2017

(65) Prior Publication Data
US 2019/0002862 A1 Jan. 3, 2019

(30) Foreign Application Priority Data
Jan. 21, 2016 (EP) .................................. 16152267

(51) Int. Cl.
*C12N 1/21* (2006.01)
*C12N 9/52* (2006.01)
*C12N 9/54* (2006.01)
*C12N 15/55* (2006.01)
*C12N 15/75* (2006.01)

(52) U.S. Cl.
CPC ................. *C12N 9/54* (2013.01); *C12N 9/52* (2013.01); *C12N 15/75* (2013.01); *C12Y 111/01006* (2013.01); *C12Y 111/01007* (2013.01); *C12Y 301/01003* (2013.01); *C12Y 301/01074* (2013.01); *C12Y 302/01001* (2013.01); *C12Y 302/01002* (2013.01); *C12Y 302/01004* (2013.01); *C12Y 302/01015* (2013.01); *C12Y 302/01025* (2013.01); *C12Y 302/01151* (2013.01); *C12Y 302/01176* (2013.01); *C12Y 304/21* (2013.01)

(58) Field of Classification Search
None
See application file for complete search history.

(56) References Cited

U.S. PATENT DOCUMENTS

2004/0147008 A1* 7/2004 Draborg ................... C12N 9/54
435/226

FOREIGN PATENT DOCUMENTS

WO 2016/069548 A2 5/2016

OTHER PUBLICATIONS

Uniprot, Accession No. A0A1G9SYT7, 2017, www.uniprot.org.*
El-Rahman et al. ("Two novel psychrotolerant species, *Bacillus psychrotolerans* sp. nov. and *Bacillus psychrodurans* sp. nov., which contain ornithine in their cell walls," Int. J. System. Evol. Microbiol., 2002, 52, 2127-22.*
Krishnamurthi et al., *Psychrobacillus* gen. nov. and proposal for reclassification of Bacillus insolitus Larkin & Stokes, 1967, B. psychrotolerans Abd-El Rahman et al., Systematic Appl. Microbiol., 2010, 33, 367-72.*
Uniprot, Accession No. A0A1I5Z7R7, 2019, www.uniprot.org.*
Uniprot, Accession No. Uniprot A0A1I5V8P7, 2017, www.uniprot.org.*
Recombinant DNA. (1992). In C. G. Morris (Ed.), Academic Press Dictionary of Science and Technology (4th ed.). Oxford, UK: Elsevier Science & Technology. Retrieved from search.credoreference.com/content/entry/apdst/recombinant_dna/0?institutionId=743.*
Baati et al, 2009, Curr Microbiol, vol. 60, No. 3, pp. 157-161.
Goh et al, 2015, Uniprot accession No. A0A0C2VYQ0.
Liu et al, 2015, Uniprot accession No. A0A0M4G5V0.
Liu et al, 2016, Uniprot accession No. A0A0Q3TX20.
Shivaji et al, 2011, Extremophiles, vol. 15, No. 1, pp. 1-22.
Vollu et al, 2014, Polar biology, vol. 37, No. 8, pp. 1121-1131.
Wati et al, 1998, EBI Accession No. U32628.

* cited by examiner

*Primary Examiner* — Robert B Mondesi
*Assistant Examiner* — Todd M Epstein
(74) *Attorney, Agent, or Firm* — David Fazzolare

(57) ABSTRACT

The present invention relates to isolated polypeptides having protease activity, and polynucleotides encoding the polypeptides. The invention also relates to nucleic acid constructs, vectors, and host cells comprising the polynucleotides as well as methods of producing and using the polypeptides.

14 Claims, No Drawings
Specification includes a Sequence Listing.

POLYPEPTIDES HAVING PROTEASE ACTIVITY AND POLYNUCLEOTIDES ENCODING SAME

CROSS-REFERENCE TO RELATED APPLICATIONS

This application is a 35 U.S.C. 371 national application of international application no. PCT/EP2017/051142 filed Jan. 20, 2017 which claims priority or the benefit under 35 U.S.C. 119 of European application no. 16152267.7 filed Jan. 21, 2016, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

The present invention relates to isolated polypeptides having protease activity and isolated nucleic acid sequences encoding the proteases. The invention also relates to nucleic acid constructs, vectors, and host cells, including plant and animal cells, comprising the nucleic acid sequences, as well as methods for producing and using the proteases, in particular the use of the proteases in detergents.

DESCRIPTION OF THE RELATED ART

The present invention provides polypeptides having protease activity and polynucleotides encoding the polypeptides.

The detergent industry has for many years implemented different enzymes in detergent formulations, most commonly used enzymes includes proteases, amylases and lipases each adapted for removing various types of stains. In addition to the enzymes detergent compositions typically include a complex combination of ingredients. For example, most cleaning products include surfactant system, bleaching agents or builders. Despite the complexity of current detergents, there remains a need for developing new detergent compositions comprising new enzymes and/or enzyme blends.

Traditionally laundering has been done at elevated temperatures and well known detergents have been selected to perform at higher temperatures.

The increased focus on improving the washing processes in order to make them more environmental friendly has resulted in a global tendency to lowering wash time, pH and temperature and decreasing the amount of detergent components which may influence the environment negatively. There is therefore a desire e.g. to launder at lower temperature and therefore a need for detergent proteases having high performance at low temperature conditions.

An uncharacterized protein from *Jeotgalibacillus campisalis* (UNIPROT:A0A0C2VYQ0) is 84% identical to the mature protease shown herein in SEQ ID NO: 2 and 89% identical to the mature protease shown herein in SEQ ID NO: 4. The mature proteases in SEQ ID NO: 2 and SEQ ID NO: 4 are 85.6% identical.

SUMMARY OF THE INVENTION

The present invention relates to an isolated polypeptide having protease activity, selected from the group consisting of:

(a) a polypeptide having at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, or 100% sequence identity to the mature polypeptide of SEQ ID NO: 2, or to the mature polypeptide of SEQ ID NO: 4; and (b) a polypeptide encoded by a polynucleotide having at least 90%, at least 91%, at least 92%, at least 93%, at least 94%, at least 95%, at least 95.5%, at least 96.5%, at least 97%, at least 97.5%, at least 98%, at least 98.5%, at least 99%, at least 99.5%, or 100% sequence identity to the mature polypeptide coding sequence of SEQ ID NO: 1, or to the mature polypeptide coding sequence of SEQ ID NO: 3.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to the use of the proteases of the invention in a cleaning process, and methods of producing detergent compositions.

OVERVIEW OF SEQUENCE LISTING

SEQ ID NO: 1 is the DNA sequence of the S8 protease from *Psychrobacillus psychrodurans*

SEQ ID NO: 2 is the amino acid sequence of the S8 protease from *Psychrobacillus psychrodurans*.

SEQ ID NO: 3 the DNA sequence of the S8 protease from *Jeotgalibacillus* sp-13376.

SEQ ID NO: 4 is the amino acid sequence of the S8 protease from *Jeotgalibacillus* sp-13376.

SEQ ID NO: 5 is the amino acid sequence of the *Bacillus clausii* secretion signal.

SEQ ID NO: 6 is the amino acid sequence of the prior art detergent protease Savinase.

Definitions

Polypeptides having protease activity, or proteases, are sometimes also designated peptidases, proteinases, peptide hydrolases, or proteolytic enzymes. Proteases may be of the exo-type that hydrolyses peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Bio-chem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web (WWW) at http://www.chem.qmw.ac.uk/iubmb/enzyme/index.html.

The proteases of the invention are:

(a) proteases belonging to the EC 3.4.21. enzyme group; and/or (b) Serine proteases of the peptidase family S8;

as described in Biochem. J. 290:205-218 (1993) and in MEROPS protease database, release, 9.4 (www.merops.ac.uk). The database is described in Rawlings, N. D., Barrett, A. J. & Bateman, A. (2010) MEROPS: the peptidase database. Nucleic Acids Res 38, D227-D233.

For determining whether a given protease is a Serine protease, and a family S8 protease, reference is made to the above Handbook and the principles indicated therein. Such determination can be carried out for all types of proteases, be it naturally occurring or wild-type proteases; or genetically engineered or synthetic proteases.

The proteases of family S8 contain the catalytic triad in the order Asp, His, Ser. Mutation of any of the amino acids of the catalytic triad will result in change or loss of enzyme activity. The amino acids of the catalytic triad of the S8 protease from *Psychrobacillus psychrodurans* (SEQ ID NO: 2) are preferably positions Asp37, His74, Ser253. The amino acids of the catalytic triad of the S8 protease from *Jeotgalibacillus* sp-13376 (SEQ ID NO: 4) are preferably positions Asp37, His74, Ser253.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of protease substrates are casein, such as Azurine-Crosslinked Casein (AZCL-casein), or suc-AAPF-pNA, Examples of suitable protease assays are described in the experimental part.

The term "protease activity" means a proteolytic activity (EC 3.4.21.) that catalyzes the hydrolysis of amide bond or a protein by hydrolysis of the peptide bond that link amino acids together in a polypeptide chain. Several assays for determining protease activity are available in the art. For purposes of the present invention, protease activity may be determined using Protazyme AK tablet (cross-linked and dyed casein; from Megazyme) as described in the Examples of the present application. The polypeptides of the present invention have at least 20%, e.g., at least 40%, at least 50%, at least 60%, at least 70%, at least 80%, at least 90%, at least 95%, or at least 100% of the protease activity of the mature polypeptide of SEQ ID NO: 2 or have at least 20%, e.g., at least 40%, at least 50%, at least 60%, at least 70%, at least 80%, at least 90%, at least 95%, or at least 100% of the protease activity of the mature polypeptide of SEQ ID NO: 4.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "catalytic domain" means the region of an enzyme containing the catalytic machinery of the enzyme.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "cleaning compositions" and "cleaning formulations," refer to compositions that find use in the removal of undesired compounds from items to be cleaned, such as fabric, carpets, dishware including glassware, contact lenses, hard surfaces such as tiles, zincs, floors, and table surfaces, hair (shampoos), skin (soaps and creams), teeth (mouthwashes, toothpastes), etc. The terms encompasses any materials/compounds selected for the particular type of cleaning composition desired and the form of the product (e.g., liquid, gel, granule, or spray compositions), as long as the composition is compatible with the protease according to the invention and other enzyme(s) used in the composition. The specific selection of cleaning composition materials is readily made by considering the surface, item or fabric to be cleaned, and the desired form of the composition for the cleaning conditions during use. These terms further refer to any composition that is suited for cleaning, bleaching, disinfecting, and/or sterilizing any object and/or surface. It is intended that the terms include, but are not limited to detergent composition (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types.

The terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. It is intended that in addition to the protease according to the invention, the term encompasses detergents that contains, e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti corrosion agents, enzyme inhibitors or stabilizers, enzyme activators, transferase(s), hydrolytic enzymes, oxido reductases, bluing agents and fluorescent dyes, antioxidants, polymers and solubilizers.

The term "dish washing composition" refers to all forms of compositions for cleaning hard surfaces. The present invention is not restricted to any particular type of dish wash composition or any particular detergent.

The term "enzyme detergency benefit" or "detergency" is defined herein as the advantageous effect an enzyme may add to a detergent compared to the same detergent without the enzyme. Important detergency benefits which can be provided by enzymes are stain removal with no or very little visible soils after washing and or cleaning, prevention or reduction of redeposition of soils released in the washing process an effect that also is termed anti-redeposition, restoring fully or partly the whiteness of textiles, which originally were white but after repeated use and wash have obtained a greyish or yellowish appearance an effect that also is termed whitening. Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric an effect that is also termed dye transfer inhibition or anti-backstaining, removal of protruding or broken fibers from a fabric surface to decrease pilling tendencies or remove already existing pills or fuzz an effect that also is termed anti-pilling, improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching component such as hydrogen peroxide or other peroxides.

The term "expression" includes any step involved in the production of a polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to control sequences that provide for its expression.

The term "fabric" encompasses any textile material. Thus, it is intended that the term encompass garments, as well as fabrics, yarns, fibers, non-woven materials, natural materials, synthetic materials, and any other textile material.

The term "fragment" means a polypeptide having one or more (e.g., several) amino acids absent from the amino and/or carboxyl terminus of a mature polypeptide or domain; wherein the fragment has protease activity.

The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics, metals, china, glass and acrylics.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "improved wash performance" is defined herein as an enzyme such as a protease (also a blend of enzymes, not necessarily only variants but also backbones, and in combination with certain cleaning composition etc.) displaying an alteration of the wash performance of e.g. said protease relative to the wash performance of the another protease or parent protease e.g. by increased stain removal. The term "wash performance" includes wash performance in laundry but also e.g. in dish wash.

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 313 of SEQ ID NO: 2.

In another aspect, the mature polypeptide is amino acids 1 to 313 of SEQ ID NO: 4.

It is known in the art that a host cell may produce a mixture of two of more different mature polypeptides (i.e., with a different C-terminal and/or N-terminal amino acid) expressed by the same polynucleotide.

The term "mature polypeptide coding sequence" means a polynucleotide that encodes a mature polypeptide having protease activity. In another aspect, the mature polypeptide coding sequence is nucleotides 343 to 1281 of SEQ ID NO: 1. In one aspect, the mature polypeptide coding sequence is nucleotides 322 to 1260 of SEQ ID NO: 3.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term "operably linked" means a configuration in which a control sequence is placed at an appropriate position relative to the coding sequence of a polynucleotide such that the control sequence directs expression of the coding sequence.

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

The term "subsequence" means a polynucleotide having one or more (e.g., several) nucleotides absent from the 5' and/or 3' end of a mature polypeptide coding sequence; wherein the subsequence encodes a fragment having protease activity.

The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabbit and silk or synthetic polymer such as nylon, aramid, polyester, acrylic, polypropylene and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used it is intended to include the broader term textiles as well.

The term "textile care benefits", which are not directly related to catalytic stain removal or prevention of redeposition of soils, are also important for enzyme detergency benefits. Examples of such textile care benefits are prevention or reduction of dye transfer from one textile to another textile or another part of the same textile an effect that is also termed dye transfer inhibition or anti-backstaining, removal of protruding or broken fibers from a textile surface to decrease pilling tendencies or remove already existing pills or fuzz an effect that also is termed anti-pilling, improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species.

The term "variant" means a polypeptide having protease activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g. several) amino acids, e.g. 1-5 amino acids adjacent to and immediately following the amino acid occupying a position.

The term "wash performance" is used as an enzyme's ability to remove stains present on the object to be cleaned during e.g. wash or hard surface cleaning.

DETAILED DESCRIPTION OF THE INVENTION

In an aspect, the present invention relates to an isolated polypeptide having a sequence identity to the mature polypeptide of SEQ ID NO: 2 of at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, or 100%, which have protease activity. In one embodiment, the polypeptide differ by no more than 20 amino acids, e.g., 1, 2, 3, 4, 5, 6, 7, 8, 9, 10, 11, 12, 13, 14, 15, 16, 17, 18 or 19 from the mature polypeptide of SEQ ID NO: 2.

In another aspect, the present invention relates to an isolated polypeptide having a sequence identity to the mature polypeptide of SEQ ID NO: 4 of at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, or 100%, which have protease activity. In one embodiment, the polypeptide differ by no more than 20 amino acids, e.g., 1, 2, 3, 4, 5, 6, 7, 8, 9, 10, 11, 12, 13, 14, 15, 16, 17, 18 or 19 from the mature polypeptide of SEQ ID NO: 4.

A polypeptide of the present invention preferably comprises or consists of the amino acid sequence of SEQ ID NO: 2, or of the amino acid sequence of SEQ ID NO: 4, or an allelic variant thereof; or is a fragment thereof having protease activity. In another aspect, the polypeptide comprises or consists of the mature polypeptide of SEQ ID NO: 2, or of the amino acid sequence of SEQ ID NO: 4. In another aspect, the polypeptide comprises or consists of amino acids 1 to 313 of SEQ ID NO: 2, or comprises or consists of amino acids 1 to 313 of SEQ ID NO: 4

In another embodiment, the present invention relates to an isolated polypeptide having protease activity encoded by a polynucleotide that hybridizes under high stringency conditions, or very high stringency conditions with the mature polypeptide coding sequence of SEQ ID NO: 1, or with the mature polypeptide coding sequence of SEQ ID NO: 3, or the full-length complement thereof (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NO: 2 or a fragment thereof, or the polynucleotide of SEQ ID NO: 3 or a subsequence thereof, as well as the polypeptide of SEQ ID NO: 4 or a fragment thereof, may be used to design nucleic acid probes to identify and clone DNA encoding polypeptides having protease activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having protease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, or with SEQ ID NO: 3 or a subsequence thereof, the carrier material is used in a Southern blot.

For purposes of the present invention, hybridization indicates that the polynucleotide hybridizes to a corresponding labeled nucleic acid probe under very low to very high stringency conditions. Molecules to which the nucleic acid probe hybridizes under these conditions can be detected using, for example, X-ray film or any other detection means known in the art.

In another embodiment, the present invention relates to an isolated polypeptide having protease activity encoded by a polynucleotide having a sequence identity to the mature polypeptide coding sequence of SEQ ID NO: 1, or to the mature polypeptide coding sequence of SEQ ID NO: 3 of at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, or variants of the mature polypeptide of SEQ ID NO: 4, comprising a substitution, deletion, and/or insertion at one or more (e.g., several) positions. In an embodiment, the number of amino acid substitutions, deletions and/or insertions introduced into the mature polypeptide of SEQ ID NO: 2, or into the mature polypeptide of SEQ ID NO: 4, is not more than 20, e.g., 1, 2, 3, 4, 5, 6, 7, 8, 9, 10, 11, 12, 13, 14, 15, 16, 17, 18, or 19. In another embodiment, the number of positions comprising a substitution, deletion, and/or insertion in the mature polypeptide of SEQ ID NO: 2 or in the mature polypeptide of SEQ ID NO: 4 is between 1 and 20, such as 1-15, 1-10 or 1-5 positions. In an embodiment, the number of positions comprising a substitution, deletion, and/or insertion in the mature polypeptide of SEQ ID NO: 2, or in the mature polypeptide of SEQ ID NO: 4, is not more than 10, e.g., 1, 2, 3, 4, 5, 6, 7, 8, 9 or 10. In another embodiment, the number of substitutions, deletions, and/or insertions in the mature polypeptide of SEQ ID NO: 2, or in the mature polypeptide of SEQ ID NO: 4 is not more than 10, e.g., 1, 2, 3, 4, 5, 6, 7, 8, 9 or 10. In a further embodiment, the number of substitutions in the mature polypeptide of SEQ ID NO: 2, or in the mature polypeptide of SEQ ID NO: 4 is not more than 10, e.g., 1, 2, 3, 4, 5, 6, 7, 8, 9 or 10. In a further embodiment, the number of conservative substitutions in the mature polypeptide of SEQ ID NO: 2, or in the mature polypeptide of SEQ ID NO: 4, is not more than 10, e.g., 1, 2, 3, 4, 5, 6, 7, 8, 9 or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant variant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Embodiments

In certain embodiments of the invention, the protease of the invention exhibits beneficial thermal properties such as thermostability, steam stability, pH properties, such as acid stability, etc.

Acidity/Alkalinity Properties

In certain embodiments of the invention, the protease of the invention exhibits beneficial properties in respect of pH, such as acid stability etc. Stability of the protease at a high pH is beneficial for cleaning and washing since detergent compositions often have an alkaline pH. The proteases of the invention exhibit surprising pH properties, especially pH stability properties which makes them interesting candidates for use in detergents.

Wash Performance

In certain embodiments of the invention, the protease of the invention exhibits beneficial wash performance. Thus a detergent with an S8 protease of the invention is more effective at removing stains compared to detergent without any protease.

Sources of Polypeptides Having Protease Activity

A polypeptide having protease activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. In one aspect, the polypeptide is a protease from a bacterium of the class Bacilli, such as from the order Bacillales, or from the family Bacilliaceae, or from the genera *Psychrobacillus* or from the genera *Jeotgalibacillus*. In an aspect, the polypeptide is a *Psychrobacillus psychrodurans* polypeptide. In another aspect, the polypeptide is a *Jeotgalibacillus* sp-13376 polypeptide.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL). The strain used is publically available under the accession number ATCC 31203 or DSM 43911.

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Dactylosporangium*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, or on the basis of the polynucleotide presented as the mature polypeptide coding sequence of SEQ ID NO: 3, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, Bacillus, Clostridium, Enterococcus, Geobacillus, Lactobacillus, Lactococcus, Oceanobacillus, Staphylococcus, Streptococcus, and Streptomyces. Gram-negative bacteria include, but are not limited to, Campylobacter, E. coli, Flavobacterium, Fusobacterium, Helicobacter, Ilyobacter, Neisseria, Pseudomonas, Salmonella, and Ureaplasma.

The bacterial host cell may be any Bacillus cell including, but not limited to, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, and Bacillus thuringiensis cells.

The bacterial host cell may also be any Streptococcus cell including, but not limited to, Streptococcus equisimilis, Streptococcus pyogenes, Streptococcus uberis, and Streptococcus equi subsp. Zooepidemicus cells.

The bacterial host cell may also be any Streptomyces cell including, but not limited to, Streptomyces achromogenes, Streptomyces avermitilis, Streptomyces coelicolor, Streptomyces griseus, and Streptomyces lividans cells.

The introduction of DNA into a Bacillus cell may be effected by protoplast transformation (see, e.g., Chang and Cohen, 1979, Mol. Gen. Genet. 168: 111-115), competent cell transformation (see, e.g., Young and Spizizen, 1961, J. Bacteriol. 81: 823-829, or Dubnau and Davidoff-Abelson, 1971, J. Mol. Biol. 56: 209-221), electroporation (see, e.g., Shigekawa and Dower, 1988, Biotechniques 6: 742-751), or conjugation (see, e.g., Koehler and Thorne, 1987, J. Bacteriol. 169: 5271-5278). The introduction of DNA into an E. coli cell may be effected by protoplast transformation (see, e.g., Hanahan, 1983, J. Mol. Biol. 166: 557-580) or electroporation (see, e.g., Dower et al., 1988, Nucleic Acids Res. 16: 6127-6145). The introduction of DNA into a Streptomyces cell may be effected by protoplast transformation, electroporation (see, e.g., Gong et al., 2004, Folia Microbiol. (Praha) 49: 399-405), conjugation (see, e.g., Mazodier et al., 1989, J. Bacteriol. 171: 3583-3585), or transduction (see, e.g., Burke et al., 2001, Proc. Natl. Acad. Sci. USA 98: 6289-6294). The introduction of DNA into a Pseudomonas cell may be effected by electroporation (see, e.g., Choi et al., 2006, J. Microbiol. Methods 64: 391-397) or conjugation (see, e.g., Pinedo and Smets, 2005, Appl. Environ. Microbiol. 71: 51-57). The introduction of DNA into a Streptococcus cell may be effected by natural competence (see, e.g., Perry and Kuramitsu, 1981, Infect. Immun. 32: 1295-1297), protoplast transformation (see, e.g., Catt and Jollick, 1991, Microbios 68: 189-207), electroporation (see, e.g., Buckley et al., 1999, Appl. Environ. Microbiol. 65: 3800-3804), or conjugation (see, e.g., Clewell, 1981, Microbiol. Rev. 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a Candida, Hansenula, Kluyveromyces, Pichia, Saccharomyces, Schizosaccharomyces, or Yarrowia cell, such as a Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, or Yarrowia lipolytica cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

The filamentous fungal host cell may be an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

For example, the filamentous fungal host cell may be an Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum,

*Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Psychrobacillus* cell. In a more preferred aspect, the cell is a *Psychrobacillus psychrodurans* cell. In another preferred aspect, the cell is a *Jeotgalibacillus* cell. In a more preferred aspect, the cell is a *Jeotgalibacillus* sp-13376 cell.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Signal Peptide and Propeptide

The present invention also relates to an isolated polynucleotide encoding a signal peptide comprising or consisting of amino acids −114 to −86 of SEQ ID NO: 2. The present invention also relates to an isolated polynucleotide encoding a propeptide comprising or consisting of amino acids −85 to −1 of SEQ ID NO: 2. The present invention also relates to an isolated polynucleotide encoding a signal peptide and a propeptide comprising or consisting of amino acids −114 to −1 of SEQ ID NO: 2. The polynucleotides may further comprise a gene encoding a protein, which is operably linked to the signal peptide and/or propeptide. The protein is preferably foreign to the signal peptide and/or propeptide. In one aspect, the polynucleotide encoding the signal peptide is nucleotides 1 to 87 of SEQ ID NO: 1. In another aspect, the polynucleotide encoding the propeptide is nucleotides 88 to 342 of SEQ ID NO: 1. In another aspect, the polynucleotide encoding the signal peptide and the propeptide is nucleotides 1 to 342 of SEQ ID NO: 1.

The present invention also relates to an isolated polynucleotide encoding a signal peptide comprising or consisting of amino acids −107 to −82 of SEQ ID NO: 4. The present invention also relates to an isolated polynucleotide encoding a propeptide comprising or consisting of amino acids −81 to −1 of SEQ ID NO: 4. The present invention also relates to an isolated polynucleotide encoding a signal peptide and a propeptide comprising or consisting of amino acids −107 to −1 of SEQ ID NO: 4. The polynucleotides may further comprise a gene encoding a protein, which is operably linked to the signal peptide and/or propeptide. The protein is preferably foreign to the signal peptide and/or propeptide. In one aspect, the polynucleotide encoding the signal peptide is nucleotides 1 to 78 of SEQ ID NO: 3. In another aspect, the polynucleotide encoding the propeptide is nucleotides 79 to 321 of SEQ ID NO: 3. In another aspect, the polynucleotide encoding the signal peptide and the propeptide is nucleotides 1 to 321 of SEQ ID NO: 3.

The present invention also relates to nucleic acid constructs, expression vectors and recombinant host cells comprising such polynucleotides.

Enzyme Compositions

The present invention also relates to compositions comprising a polypeptide of the present invention.

Fermentation Broth Formulations or Cell Compositions

A composition may be a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

Detergent Compositions

In one embodiment, the invention is directed to compositions comprising a polypeptide of the present invention in combination with one or more additional cleaning composition components. Thus one embodiment, the present invention relates to a detergent composition comprising an isolated polypeptide having a sequence identity to the mature polypeptide of SEQ ID NO: 2 of at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, or 100%, which have protease activity.

In a further embodiment, the present invention relates to a detergent composition comprising an isolated polypeptide having a sequence identity to the mature polypeptide of SEQ ID NO: 4 of at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, or 100%, which have protease activity.

The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product.

Although components mentioned below are categorized by general header according to a particular functionality, this is not to be construed as a limitation, as a component may comprise additional functionalities as will be appreciated by the skilled artisan.

In one embodiment of the present invention, the a polypeptide of the present invention may be added to a detergent composition in an amount corresponding to 0.001-200 mg of protein, such as 0.005-100 mg of protein, preferably 0.01-50 mg of protein, more preferably 0.05-20 mg of protein, even more preferably 0.1-10 mg of protein per liter of wash liquor.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO92/19709 and WO92/19708 or the polypeptides according to the invention may be stabilized using peptide aldehydes or ketones such as described in WO 2005/105826 and WO 2009/118375.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 1% to about 40% by weight of a cationic surfactant. Non-limiting examples of cationic surfactants include alklydimethylehanolamine quat (ADMEAQ), cetyltrimethylammonium bromide (CTAB), dimethyldistearylammonium chloride (DSDMAC), alkylbenzyldimethylammonium, alkyl quaternary ammonium compounds, alkoxylated quaternary ammonium (AQA), and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 1% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 1% to about 40% by weight of a zwitterionic surfactant. Non-limiting examples of zwitterionic surfactants include betaine, alkyldimethylbetaine, and sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2''-nitrilotriethanol), and carboxymethyl inulin (CMI), and combinations thereof.

The detergent composition may also contain 0-65% by weight, such as about 5% to about 40%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2''-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), ethylenediaminetetra(methylenephosphonic acid) (HEDP), ethylenediaminetetra(methylenephosphonic acid) (EDTMPA), diethylenetriaminepenta(methylenephosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)aspartic acid (SMAS), N-(2-sulfoethyl)aspartic acid (SEAS), N-(2-sulfomethyl)glutamic acid (SMGL), N-(2-sulfoethyl)glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)-ethylidenediamine-N,N',N'-triacetate (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053.

Bleaching Systems

The detergent may contain 0-10% by weight, such as about 1% to about 5%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides, Suitable examples are tetracetylethylene diamine (TAED), sodium 4-[(3,5,5-trimethylhexanoyl)oxy]benzene sulfonate (ISONOBS), diperoxy dodecanoic acid, 4-(dodecanoyloxy)benzenesulfonate (LOBS), 4-(decanoyloxy)benzenesulfonate, 4-(decanoyloxy)benzoate (DOBS), 4-(nonanoyloxy)benzenesulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like Triacin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

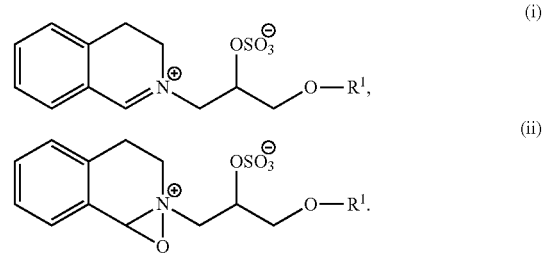

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO2007/087258, WO2007/087244, WO2007/087259, WO2007/087242. Suitable photobleaches may for example be sulfonated zinc phthalocyanine Polymers The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments which when formulated in detergent compositions can deposit onto a fabric when said fabric is contacted with a wash liquor comprising said detergent compositions thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257, WO2007/087243.

Additional Enzymes

The detergent additive as well as the detergent composition may comprise one or more enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/001544.

Other cellulases are endo-beta-1,4-glucanase enzyme having a sequence of at least 97% identity to the amino acid sequence of position 1 to position 773 of SEQ ID NO: 2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Proteases: Suitable proteases to be used with the protease of the invention include those of bacterial, fungal, plant, viral or animal origin e.g. vegetable or microbial origin. Microbial origin is preferred. Chemically modified or protein engineered variants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellulomonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus Lentus* protease shown in SEQ ID NO 1 of WO 2016/001449. More preferred the subtilase variants may comprise the mutations: S3T, V4I, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A, R269H. The protease variants are preferably variants of the *Bacillus lentus* protease (Savinase®) shown in SEQ ID NO 1 of WO 2016/001449, the *Bacillus amylolichenifaciens* protease (BPN') shown in SEQ ID NO 2 of WO2016/001449. The protease variants preferably have at least 80% sequence identity to SEQ ID NO 1 or SEQ ID NO 2 of WO 2016/001449.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases: Suitable lipases and cutinases include those of bacterial or fungal origin. Chemically modified or protein engineered variant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyl transferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases: Suitable amylases which can be used together with the protease of the invention may be an alpha-amylase or a glucoamylase and may be of bacterial or fungal origin. Chemically modified or protein engineered variants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefa-*

*ciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases: Suitable peroxidases/oxidases include those of plant, bacterial or fungal origin. Chemically modified or protein engineered variants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants—The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents—The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent—The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate; 4,4'-bis-(2,4-dianilino-s-triazin-6-ylamino) stilbene-2.2'-disulfonate; 4,4'-bis-(2-anilino-4-(N-methyl-N-2-hydroxy-ethylamino)-s-triazin-6-ylamino) stilbene-2,2'-disulfonate, 4,4'-bis-(4-phenyl-2,1,3-triazol-2-yl)stilbene-2,2'-disulfonate; 4,4'-bis-(2-anilino-4(1-methyl-2-hydroxy-ethylamino)-s-triazin-6-ylamino) stilbene-2,2'-disulfonate and sodium 5-(2H-naphtho[1,2-d][1,2,3]triazol-2-yl)-2-[(E)-2-phenylvinyl]-benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil release polymers—The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalate based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents—The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

Formulation of Detergent Products

The detergent composition of the invention may be in any convenient form, e.g., a bar, a homogenous tablet, a tablet having two or more layers, a regular or compact powder, a granule, a paste, a gel, or a regular, compact or concentrated liquid.

Detergent formulation forms: Layers (same or different phases), Pouches, versus forms for Machine dosing unit.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

Definition/Characteristics of the Forms:

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Laundry Soap Bars

The polypeptides of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g. a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, an enzyme, optionally one or more additional enzymes, a protease inhibitor, and a salt of a monovalent cation and an organic anion may be prepared and the mixture is then plodded. The enzyme and optional additional enzymes may be added at the same time as the protease inhibitor for example in liquid form. Besides the mixing step and the plodding step, the process may further comprise the steps of milling, extruding, cutting, stamping, cooling and/or wrapping.

Uses

The present invention is also directed to methods for using the protease according to the invention or compositions thereof in laundry of textiles and fabrics, such as house hold laundry washing and industrial laundry washing.

The invention is also directed to methods for using the compositions thereof in hard surface cleaning such as Automated Dish Washing (ADW), car wash and cleaning of Industrial surfaces. Thus one embodiment, the present invention relates to the use in cleaning such as laundry or dish wash of a protease according to the invention or a detergent composition comprising a protease according to the present invention having a sequence identity to the mature polypeptide of SEQ ID NO: 2 or to the mature polypeptide of SEQ ID NO: 4. Thus in one embodiment, the present invention relates to the use of an isolated polypeptide having a sequence identity to the mature polypeptide of SEQ ID NO: 2 of at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, or 100% which have protease activity in a detergent, a cleaning process and/or laundry process.

In a further embodiment, the present invention relates to the use of an isolated polypeptide having a sequence identity to the mature polypeptide of SEQ ID NO: 4 of at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, or 100% which have protease activity in a detergent, a cleaning process and/or laundry process.

The polypeptides of the present invention may be added to and thus become a component of a detergent composition. The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the present invention as described herein.

The soils and stains that are important for detergent formulators are composed of many different substances, and a range of different enzymes, all with different substrate specificities have been developed for use in detergents both in relation to laundry and hard surface cleaning, such as dishwashing. These enzymes are considered to provide an enzyme detergency benefit, since they specifically improve stain removal in the cleaning process they are applied in as compared to the same process without enzymes. Stain removing enzymes that are known in the art include enzymes such as carbohydrases, amylases, proteases, lipases, cellulases, hemicellulases, xylanases, cutinases, and pectinase.

In one aspect, the present invention concerns the use of an isolated polypeptide having a sequence identity to the mature polypeptide of SEQ ID NO: 2 of at least 90%, at least 91%, at least 92%, at least 93%, at least 94%, at least 95%, at least 96%, at least 97%, at least 98%, at least 99%, or 100% in detergent compositions and cleaning processes, such as laundry and hard surface cleaning.

In a further aspect, the present invention concerns the use of an isolated polypeptide having a sequence identity to the mature polypeptide of SEQ ID NO: 4 of at least 90%, at least 91%, at least 92%, at least 93%, at least 94%, at least 95%, at least 96%, at least 97%, at least 98%, at least 99%, or 100% in detergent compositions and cleaning processes, such as laundry and hard surface cleaning.

In a preferred aspect of the present invention, the protease of the invention useful according to the invention may be combined with at least two enzymes. These additional enzymes are described in details in the section "other enzymes" more preferred at least three, four or five enzymes. Preferably, the enzymes have different substrate specificity, e.g., carbolytic activity, proteolytic activity, amylolytic activity, lipolytic activity, hemicellulytic activity or pectolytic activity. The enzyme combination may for example be a protease of the invention with another stain removing enzyme, e.g., a protease of the invention and an amylase, a protease of the invention and a cellulase, a protease of the invention and a hemicellulase, a protease of the invention and a lipase, a protease of the invention and a cutinase, a protease of the invention and a pectinase or a protease of the invention and an anti-redeposition enzyme. More preferably, the protease of the invention is combined with at least two other stain removing enzymes, e.g., a protease of the invention, a lipase and an amylase; or a protease of the invention, an amylase and a pectinase; or a protease of the invention, an amylase and a cutinase; or a protease of the invention, an amylase and a cellulase; or a protease of the invention, an amylase and a hemicellulase; or a protease of the invention, a lipase and a pectinase; or a protease of the invention, a lipase and a cutinase; or a protease of the invention, a lipase and a cellulase; or a protease of the invention, a lipase and a hemicellulase. Even more preferably, a protease of the invention may be combined with at least three other stain removing enzymes, e.g., a protease of the invention, an amylase, a lipase and a pectinase; or a protease of the invention, an amylase, a lipase and a cutinase; or a protease of the invention, an amylase, a lipase and a cellulase; or a protease of the invention, an amylase, a lipase and a hemicellulase. A protease of the invention may be combined with any of the enzymes selected from the non-exhaustive list comprising: carbohydrases, such as an amylase, a hemicellulase, a pectinase, a cellulase, a xanthanase or a pullulanase, a peptidase, other proteases or a lipase.

In another embodiment of the present invention, a protease of the invention may be combined with one or more metalloproteases, such as a M4 Metalloprotease, including Neutrase™ or Thermolysin. Such combinations may further comprise combinations of the other detergent enzymes as outlined above.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one protease of the invention. The cleaning process or a textile care process can for example be carried out in a machine washing process or in a manual washing process. The washing solution can for example be an aqueous washing solution containing a detergent composition.

The fabrics and/or garments subjected to a washing, cleaning or textile care process of the present invention may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabbit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which are derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

The invention further concerns the use of proteases of the invention a proteinaceous stain removing processes. The proteinaceous stains may be stains such as food stains, e.g., baby food, sebum, cocoa, egg, blood, milk, ink, grass, or a combination hereof.

Typical detergent compositions includes various components in addition to the enzymes, these components have different effects, some components like the surfactants lower the surface tension in the detergent, which allows the stain being cleaned to be lifted and dispersed and then washed away, other components like bleach systems removes discolor often by oxidation and many bleaches also have strong bactericidal properties, and are used for disinfecting and sterilizing. Yet other components like builder and chelator softens, e.g., the wash water by removing the metal ions form the liquid.

In a particular embodiment, the invention concerns the use of a composition comprising a protease of the invention, wherein said enzyme composition further comprises at least one or more of the following a surfactant, a builder, a chelator or chelating agent, bleach system or bleach component in laundry or dish wash.

In a preferred embodiment of the invention, the amount of a surfactant, a builder, a chelator or chelating agent, bleach system and/or bleach component are reduced compared to amount of surfactant, builder, chelator or chelating agent, bleach system and/or bleach component used without the added protease of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of protease of the invention, such as a conventional amount of such component. In one aspect, the protease of the invention is used in detergent compositions wherein said composition is free of at least one component which is a surfactant, a builder, a chelator or chelating agent, bleach system or bleach component and/or polymer.

Washing Method

The detergent compositions comprising a protease of the present invention are ideally suited for use in laundry applications. Accordingly, the present invention includes a method for laundering a fabric. The method comprises the steps of contacting a fabric to be laundered with a cleaning laundry solution comprising the detergent composition according to the invention. The fabric may comprise any fabric capable of being laundered in normal consumer use conditions. The solution preferably has a pH of from about 5.5 to about 9. The compositions may be employed at concentrations of from about 100 ppm, preferably 500 ppm to about 15,000 ppm in solution. The water temperatures typically range from about 5° C. to about 90° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The present invention relates to a method of cleaning a fabric, a dishware or hard surface with a detergent composition comprising a protease of the invention.

A preferred embodiment concerns a method of cleaning, said method comprising the steps of: contacting an object with a cleaning composition comprising a protease of the invention under conditions suitable for cleaning said object. In a preferred embodiment the cleaning composition is a detergent composition and the process is a laundry or a dish wash process.

Still another embodiment relates to a method for removing stains from fabric which comprises contacting said a fabric with a composition comprising a protease of the invention under conditions suitable for cleaning said object.

In a preferred embodiment, the compositions for use in the methods above further comprises at least one additional enzyme as set forth in the "other enzymes" section above, such as an enzyme selected from the group consisting of carbohydrases, peptidases, proteases, lipases, cellulase, xylanases or cutinases or a combination hereof. In yet another preferred embodiment the compositions comprises a reduced amount of at least one or more of the following components a surfactant, a builder, a chelator or chelating agent, bleach system or bleach component or a polymer.

Also contemplated are compositions and methods of treating fabrics (e.g., to desize a textile) using one or more of the protease of the invention. The protease can be used in any fabric-treating method which is well known in the art (see, e.g., U.S. Pat. No. 6,077,316). For example, in one aspect, the feel and appearance of a fabric is improved by a method comprising contacting the fabric with a protease in a solution. In one aspect, the fabric is treated with the solution under pressure.

In one embodiment, the protease is applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The protease can be applied to remove these sizing protein or protein derivatives. After the textiles have been woven, a fabric can proceed to a desizing stage. This can be followed by one or more additional fabric processing steps. Desizing is the act of removing size from textiles. After weaving, the size coating should be removed before further processing the fabric in order to ensure a homogeneous and wash-proof result. Also provided is a method of desizing comprising enzymatic hydrolysis of the size by the action of an enzyme.

Low Temperature Uses

One embodiment of the invention concerns a method of doing laundry, dish wash or industrial cleaning comprising contacting a surface to be cleaned with a protease of the invention, and wherein said laundry, dish wash, industrial or institutional cleaning is performed at a temperature of about 40° C. or below. One embodiment of the invention relates to the use of a protease of the invention in laundry, dish wash or a cleaning process wherein the temperature in laundry, dish wash, industrial cleaning is about 40° C. or below.

In another embodiment, the invention concerns the use of a protease of the invention in a protein removing process, wherein the temperature in the protein removing process is about 40° C. or below.

Thus, one aspect of the invention concerns the use of a polypeptide having a sequence identity to the mature polypeptide of SEQ ID NO: 2 of at least 90%, at least 91%, at least 92%, at least 93%, at least 94%, at least 95%, at least 96%, at least 97%, at least 98%, at least 99%, or 100%, which have protease activity in laundry, dish wash or a cleaning process wherein the temperature in laundry, dish wash, industrial cleaning is about 40° C. or below. A further aspect of the invention concerns the use of a polypeptide having a sequence identity to the mature polypeptide of SEQ ID NO: 4 of at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, or 100%, which have protease activity in laundry, dish wash or a cleaning process wherein the temperature in laundry, dish wash, industrial cleaning is about 40° C. or below.

The present invention also relates to the use in laundry, dish wash or industrial cleaning process of a protease of the invention having at least one improved property compared to a subtilisin 309 protease with the amino acid sequence shown in SEQ ID NO: 2, or with the amino acid sequence shown in SEQ ID NO: 4 and wherein the temperature in laundry, dish wash or cleaning process is performed at a temperature of about 40° C. or below, such as e.g. about 30° C. or about 20° C.

In each of the above-identified methods and uses, the wash temperature is about 40° C. or below, such as about 39° C. or below, such as about 38° C. or below, such as about 37° C. or below, such as about 36° C. or below, such as about 35° C. or below, such as about 34° C. or below, such as about 33° C. or below, such as about 32° C. or below, such as about 31° C. or below, such as about 30° C. or below, such as about 29° C. or below, such as about 28° C. or below, such as about 27° C. or below, such as about 26° C. or below, such as about 25° C. or below, such as about 24° C. or below, such as about 23° C. or below, such as about 22° C. or below, such as about 21° C. or below, such as about 20° C. or below, such as about 19° C. or below, such as about 18° C. or below, such as about 17° C. or below, such as about 16° C. or below, such as about 15° C. or below, such as about 14° C. or below, such as about 13° C. or below, such as about 12° C. or below, such as about 11° C. or below, such as about 10° C. or below, such as about 9° C. or below, such as about 8° C. or below, such as about 7° C. or below, such as about 6° C. or below, such as about 5° C. or below, such as about 4° C. or below, such as about 3° C. or below, such as about 2° C. or below, such as about 1° C. or below.

In another preferred embodiment, the wash temperature is in the range of about 5-40° C., such as about 5-30° C., about 5-20° C., about 5-10° C., about 10-40° C., about 10-30° C., about 10-20° C., about 15-40° C., about 15-30° C., about 15-20° C., about 20-40° C., about 20-30° C., about 25-40° C., about 25-30° C., or about 30-40° C. In a particular preferred embodiment the wash temperature is about 30° C.

In particular embodiments, the low temperature washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 9.

In particular embodiments, the low temperature washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

Use in Removing Egg Stains

Another particular embodiment of the invention concerns removal of egg stains. These types of stain are often very difficult to remove completely. Egg stains are particularly problematic in hard surface cleaning such as dish wash where the stains often remain on the plates and cutlery after washing. The proteases of the invention are particularly suitable for removing egg stains.

Thus, the invention further concerns methods for removing egg stains from textiles, fabrics and/or hard surfaces like dishes and cutlery in particular from fabrics and textiles. A preferred aspect of the invention concerns a method of removing egg stains from textiles and/or fabrics comprising contacting a surface in need of removal of an egg stain with a protease of the invention. In one embodiment, the invention comprises a method of removing egg stains from textiles and/or fabrics comprising contacting a surface in need of removal of an egg stain with a detergent composition comprising a protease of the invention. The invention also concerns a method of removing egg stains comprising adding a protease of the invention to a laundry and/or washing process wherein said textiles and/or fabric comprises various egg stains.

One embodiment of the present invention relates to a method for removal of egg stains from a hard surface or from laundry, the method comprising contacting the egg stain-containing hard surface or the egg stain-containing laundry with a cleaning or detergent composition, preferably a laundry or dish wash composition, containing a protease of the invention.

Another embodiment relates a method for removing egg stains from fabric or textile which comprises contacting the fabric or textile with a cleaning or detergent composition, preferably a laundry or dish wash composition, comprising a protease of the invention.

A still further embodiment relates to a method for removing egg stains from fabric or textile which comprises contacting said a fabric or textile with a composition comprising a protease of the invention, wherein said composition further comprises at least one additional enzyme as set forth in the "other enzymes" section above, such as an enzyme selected from the group consisting of a carbohydrase, a peptidase, a protease, a lipase, a cellulase, a xylanase, a cutinase or a combination hereof.

In particular embodiments, the egg removing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, about 5.5 to about 9, preferably about 6 to about 8.5, and more preferably about 6 to about 8.

In particular embodiments, the egg removing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

Materials and Methods

Composition of Model Detergents

Wash performance of proteases was investigated in liquid detergents and powder detergents, which had the following compositions:

TABLE 1

Composition of the model detergents used in the wash experiments (amounts are stated in wt %)

| Laundry liquid model detergent LF | Natrium hydroxide 99%: 2.95%<br>Sulfonic acid: 11.52%<br>Soy fatty acid: 5.5%<br>Propylenglycol: 5.05%<br>C13-alkoholethoxylat, 8 EO: 9.45%<br>Phosphonat, Dequest 2066: 1.00%<br>Triethanolamin: 2.0%<br>Coco fatty acid: 4.5%<br>Natrium citrate, dihydrate: 1.0%<br>EtOH: 4.63%<br>Opacifier: 0.12%<br>Water to 100% |
|---|---|
| Laundry liquid model detergent J | LAS 5.15%<br>AS 5.00%<br>AEOS 14.18%<br>Coco fatty acid 1.00%<br>AEO 5.00%<br>MEA 0.30%<br>MPG 3.00<br>EtOH 1.50%<br>DTPA (Na salt) 0.25%<br>Sodium citrate 4.00%<br>Sodium formate 1.00%<br>Sodium hydroxide 0.66%<br>Water 58.95% |
| Laundry powder model detergent A | Sodium citrate dihydrate 32.3%<br>Sodium-LAS 24.2%<br>Sodium lauryl sulfate 32.2%<br>Neodol 25-7 (alcohol ethoxylate) 6.4%<br>Sodium sulfate 4.9% |

TABLE 2

Composition of the model detergent X used in the wash experiments

| Component name | Model X/kg |
|---|---|
| Na-LAS granules (Marlon ARL) | 8.25 |
| Zeolite 4A (Silkem) | 7.5 |
| Sodium disilicate (Britesil H 265 LC) | 6 |
| Sodium carbonate (dense) | 10 |
| Sokalan CP 5 Gran. | 0.5 |
| Sodium sulfate - granulate | 17.75 |
| Total | 50 |

2% AEO was added to Det X

TABLE 3

Amounts of the model detergents used in the wash experiments (amounts in wt %)

| | Liquid detergents | | | Powder detergents |
|---|---|---|---|---|
| | Det A | Det J | Det LF | Det X |
| Dosage (g/L) | 3.3 | 0.78 | 8 | 1.75 |

Test Materials

Wash performance of proteases was investigated on test materials (swatches) obtained from Center for Testmaterials BV, P.O. Box 120, 3133 KT Vlaardingen, the Netherlands and EMPA Testmaterials AG, Mövenstrasse 12, CH-9015 St. Gallen, Switzerland.

Wash Assays

Automatic Mechanical Stress Assay (AMSA) for Laundry

In order to assess the wash performance in laundry washing experiments were performed, using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid were vigorously shaken to bring the test solution in contact with the textile and apply mechanical stress in a regular, periodic oscillating manner. For further description see WO02/42740 especially the paragraph "Special method embodiments" at page 23-24.

The wash performance was measured as the brightness of the colour of the textile washed. Brightness can also be expressed as the intensity of the light reflected from the sample when illuminated with white light. When the sample is stained the intensity of the reflected light is lower, than that of a clean sample. Therefore, the intensity of the reflected light can be used to measure wash performance.

Colour measurements were made with a professional flatbed scanner (Kodak iQsmart, Kodak, Midtager 29, DK-2605 Brøndby, Denmark), which is used to capture an image of the washed textile.

To extract a value for the light intensity from the scanned images, 24-bit pixel values from the image were converted into values for red, green and blue (RGB). The intensity value (Int) was calculated by adding the RGB values together as vectors and then taking the length of the resulting vector:

$$Int = \sqrt{r^2 + g^2 + b^2}.$$

Terg-O-Tometer (TOM) Wash Assay for Laundry

The Terg-O-tometer (TOM) is a medium scale model wash system that can be applied to test 16 different wash conditions simultaneously. A TOM is basically a large temperature controlled water bath with up to 16 open metal beakers submerged into it. Each beaker constitutes one small top loader style washing machine and during an experiment, each of them will contain a solution of a specific detergent/enzyme system and the soiled and unsoiled fabrics where on which performance is tested. Mechanical stress is achieved by a rotating stirring arm, which stirs the liquid within each beaker with 120 rpm.

In a TOM experiment, factors such as the ballast to soil ratio and the fabric to wash liquor ratio can be varied. Therefore, the TOM provides the link between small scale experiments, such as AMSA, and the more time consuming full scale wash experiments in full scale washing machines.

After wash swatches are rinsed for 5 min under tab water and then dried overnight on a tray (12 h-20 h) at room temperature (around 20-25 C) and 40% humidity after wash. The next day swatches are measured at 460 nm with a Macbeth Color-Eye 7000 spectrophotometer.

Protease Assays

1) Suc-AAPF-pNA Assay:

pNA substrate: Suc-AAPF-pNA (Bachem L-1400).

Temperature: Room temperature (25° C.)

Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.

2) Protazyme AK Assay:

Substrate: Protazyme AK tablet (cross-linked and dyed casein; from Megazyme)

Temperature: controlled (assay temperature).

Assay buffers: 100 mM succinic acid, 100 mM HEPES, 100 mM CHES, 100 mM CABS, 1 mM $CaCl_2$, 150 mM KCl, 0.01% Triton X-100, pH 7.0.

A Protazyme AK tablet was suspended in 2.0 ml 0.01% Triton X-100 by gentle stirring. 500 µl of this suspension and 500 µl assay buffer were dispensed in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath. Then the tube was centrifuged in an ice cold centrifuge for a few minutes and 200 µl supernatant was transferred to a microtiter plate.

$OD_{650}$ was read as a measure of protease activity. A buffer blind was included in the assay (instead of enzyme).

EXAMPLES

Example 1

Cloning and Expression of a S8 Protease from *Psychrobacillus psychrodurans*

The protease was derived from a bacterial strain isolated from a soil sample collected in Denmark. Chromosomal DNA from a pure culture was purified and subjected to full genome sequencing using Illumina technology. The assembled genome sequence and subsequent analysis of the 16S ribosomal subunit gene sequences confirmed the identity of the strain as belonging to the species *Psychrobacillus psychrodurans*.

The genome sequence was analyzed for proteases from the MEROPS family S8 and a gene encoding a putative S8 protease with the nucleotide sequence given in SEQ ID: 1 was identified.

Example 2

Expression of the *Psychrobacillus psychrodurans* S8A Protease Gene in *Bacillus subtilis*

The gene encoding the protease was amplified by PCR and fused with regulatory elements and homology regions for recombination into the *B. subtilis* genome.

The linear integration construct was a SOE-PCR fusion product (Horton, R. M., Hunt, H. D., Ho, S. N., Pullen, J. K. and Pease, L. R. (1989) *Engineering hybrid genes without the use of restriction enzymes, gene splicing by overlap extension Gene* 77: 61-68) made by fusion of the gene between two *Bacillus subtilis* chromosomal regions along with strong promoters and a chloramphenicol resistance marker. The SOE PCR method is also described in patent application WO 2003095658.

The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

The gene was expressed with a *Bacillus clausii* secretion signal ((encoding the following amino acid sequence: MKKPLGKIVASTALLISVAFSSSIASA (SEQ ID NO: 5)) replacing the native secretion signal.

The SOE-PCR product was transformed into *Bacillus subtilis* and integrated in the chromosome by homologous recombination into the pectate lyase locus. Subsequently a recombinant *Bacillus subtilis* clone containing the integrated expression construct was grown in liquid culture. The culture broth was centrifuged (20000×g, 20 min) and the supernatant was carefully decanted from the precipitate and used for purification of the enzyme.

The supernatant was filtered through a Nalgene 0.2 μm filtration unit in order to remove the rest of the *Bacillus* host cells. The 0.2 μm filtrate was applied to a Bacitracin agarose column (from Upfront chromatography) equilibrated in 100 mM $H_3BO_3$, 10 mM MES, 2 mM $CaCl_2$, pH 6. After washing the column extensively with the equilibration buffer, the S8 protease was eluted with 100 mM $H_3BO_3$, 10 mM MES, 2 mM $CaCl_2$, 1M NaCl, pH 6 with 25% (v/v) 2-propanol. The eluted peak was transferred to 100 mM $H_3BO_3$, 10 mM MES, 2 mM $CaCl_2$, pH 6 on a G25 sephadex column (from GE Healthcare). The G25 sephadex transferred S8 protease was used for further experiments.

When this purified product was analysed by SDS-PAGE only one band was seen on the coomassie stained SDS-PAGE gel. Protease activity of the purified product was demonstrated using the Protazyme AK assay.

Example 3

Determination of Molecular Weight of the *Psychrobacillus psychrodurans* S8A Protease Intact molecular weight analysis of the purified enzyme was performed using a MAXIS II electrospray mass spectrometer (Bruker Daltonik GmbH, Bremen, DE). The samples were diluted to 0.1 mg/ml in MQ water. The diluted sample was applied to an Aeris Widepore C4 column (Phenomenex). The sample was washed and eluted from the column running an acetonitrile linear gradient and introduced to the electrospray source with a flow of 300 ml/min by an Ultimate 3000 LC system (Dionex). Data analysis was performed with DataAnalysis version 4.2 (Bruker Daltonik GmbH, Bremen, DE). The molecular weight of the sample was calculated by Maximum Entropy deconvolution of the raw data in the range 10,000 to 40,000 Da. The dominant peak observed at molecular weight of 31942.87 Da corresponds within 0.58 Da to the calculated molecular weight of the mature protease in SEQ ID NO: 2.

Example 4

Wash Performance of the *Psychrobacillus psychrodurans* S8A Protease in Automatic Mechanical Stress Assay (AMSA)

In order to assess the wash performance in laundry, washing experiments are performed using the Automatic Mechanical Stress Assay (AMSA). The laundry experiments are conducted under the experimental conditions specified below:

TABLE 4

| AMSA experimental conditions | |
|---|---|
| Test solution volume | 140 μL detergent per slot; 20 μL enzyme per slot |
| pH | As is |
| Wash time | 20 minutes |
| Temperature | 40° C. |
| Water hardness | 15°dH-$Ca^{2+}$/$Mg^{2+}$/$HCO_3^-$ 4:1:7.5 |
| Protease dosage | 0-7.5-15-30-60 nM |
| Test materials | PC-05 (Blood/milk/ink on cotton/polyester) |
| | PC-03 (Chocolate-milk/ink on cotton/polyester) |

The protease prepared in Examples 1 and 2 was tested in AMSA as described. The test was performed on different stains at 40° C. Wash performance was compared with a well known commercial detergent protease, Savinase (SEQ ID NO: 6), derived from *Bacillus lentus*. The results are shown in table 5.

TABLE 5

Delta intensities of S8A protease from *Psychrobacillus psychrodurans* and Savinase relative to the liquid detergents without protease.

| | S8A protease from *Psychrobacillus psychrodurans* | | | | Savinase | | | |
|---|---|---|---|---|---|---|---|---|
| Condition | 7.5 nM | 15 nM | 30 nM | 60 nM | 7.5 nM | 15 nM | 30 nM | 60 nM |
| Det LF, 40° C., PC-05 | 47 | 62 | 70 | 72 | 55 | 61 | 66 | 70 |
| Det LF, 40° C., PC-03 | 26 | 32 | 41 | 48 | 22 | 29 | 33 | 39 |

The results show that the *Psychrobacillus psychrodurans* S8 protease has significant wash performance in liquid detergents on different stains. On the PC-03 stain the *Psychrobacillus psychrodurans* S8 protease outperforms the protease Savinase.

Example 5

Wash Performance in Terg-O-Tometer (TOM)

In order to assess the wash performance in laundry, washing experiments are performed using the Terg-O-tometer (TOM) assay. The TOM experiments are conducted under the experimental conditions specified below:

TABLE 6

| TOM experimental conditions specified | |
|---|---|
| Test solution volume | 1000 ml |
| pH | As is |
| Wash time | 20 minutes (Det X), 30 minutes (Det A) and 12 minutes (Det J) |
| Temperature | 40° C., 30° C. and 20° C. |
| Water hardness | 6°dH-$Ca^{2+}$/$Mg^{2+}$/$HCO_3^-$ 2:1:4.5 (Det J) |
| | 9°dH-$Ca^{2+}$/$Mg^{2+}$/$HCO_3^-$ 2:1:4.5 (Det X) |
| | 15°dH-$Ca^{2+}$/$Mg^{2+}$/$HCO_3^-$ 4:1:7.5 (Det A) |
| Protease dosage | 10-30 nM and 60 nM |
| Test materials | CS-37 (Full egg with pigment non-aged on cotton) |
| | EMPA 117 (Blood/milk/ink on cotton, extra heat treated) |
| | C-05 (Blood/milk/ink on cotton) |
| | C-10 (Oil/milk/pigment on cotton) |
| | EMPA 164 (Grass on cotton) |
| | (2 swatches of 5 × 5 cm each) |
| Ballast | Cotton swatches (5 × 5 cm) from WFK80A and WFK10A in a ratio of 50/50 are added on top of the swatches to give a total weight of 30 g |

The protease from *Psychrobacillus psychrodurans* (SEQ ID NO: 2) was tested in TOM wash as described. The test was performed in a liquid and a powder detergent on several different stains at both 20° C. and 40° C. and at different protease dosages. Wash performance was compared with a well-known protease for detergent, Savinase (SEQ ID NO: 6), a protease derived from *Bacillus lentus*. The results are shown in table 7.

TABLE 7

Delta remission of S8A protease from *Psychrobacillus psychrodurans* and of Savinase relative to the liquid detergent without protease.

| | S8A protease from *Psychrobacillus psychrodurans* | | | Savinase | | |
|---|---|---|---|---|---|---|
| | Det J, 30 nM | Det A, 60 nM | | Det J, 30 nM | Det A, 60 nM | |
| | 30° C. | 20° C. | 40° C. | 30° C. | 20° C. | 40° C. |
| EMPA 117 | 16.9 | 24.5 | 39.3 | 15.5 | 24.3 | 38.4 |
| C-05 | 18.6 | 22.5 | 29.9 | 17.1 | 25.4 | 30.7 |
| PC-03 | 38.7 | 47.6 | 61.4 | 37.3 | 45.0 | 56.6 |
| CS-37 | 37.5 | 45.8 | 47.6 | 36.8 | 46.8 | 51.8 |
| EMPA164 | 38.2 | 41.5 | 48.8 | 38.0 | 40.7 | 48.0 |
| C-10 | 44.3 | 51.1 | 61.2 | 42.8 | 48.8 | 62.0 |

The results show that the *Psychrobacillus psychrodurans* S8 protease has significant wash performance in liquid detergents on several investigated stains at different temperatures and different protease concentrations. Under most investigated conditions the *Psychrobacillus psychrodurans* S8 protease has improved wash performance in comparison to the known laundry protease Savinase.

TABLE 8

Delta intensities of *Psychrobacillus psychrodurans* and Savinase relative to the powder detergent without protease.

| | S8 protease from *Psychrobacillus psychrodurans* Det X, 20° C. | | Savinase Det X, 20° C. | |
|---|---|---|---|---|
| Stain | 10 nM | 30 nM | 10 nM | 30 nM |
| EMPA 117 | 20.3 | 27.0 | 22.1 | 19.7 |
| C-05 | 30.0 | 35.7 | 32.3 | 28.1 |
| PC-03 | 41.7 | 50.3 | 45.3 | 42.3 |
| CS-37 | 51.1 | 53.0 | 51.8 | 56.5 |
| EMPA164 | 33.5 | 42.4 | 33.7 | 35.0 |

The results show that the *Psychrobacillus psychrodurans* S8 protease has significant wash performance on all investigated stains in powder detergents. Especially at a dosage of 30 nM the *Psychrobacillus psychrodurans* S8 protease has improved wash performance in comparison to the known laundry protease Savinase.

Example 6

Cloning and Expression of an S8 Protease from *Jeotgalibacillus* sp-13376

The protease was derived from a bacterial strain isolated from a soil sample collected in Ontario, Canada. Chromosomal DNA from a pure culture was purified and subjected to full genome sequencing using Illumina technology. The assembled genome sequence and subsequent analysis of the 16S ribosomal subunit gene sequences confirmed the identity of the strain as belonging to a new species within the genus *Jeotgalibacillus*. The species was named *Jeotgalibacillus* sp-13376.

The genome sequence was analyzed for proteases from the MEROPS family S8 and a gene encoding a putative S8 protease with the nucleotide sequence given in SEQ ID: 3 was identified.

Example 7

Expression of the *Jeotgalibacillus* sp S8A Protease Gene in *Bacillus subtilis*

The gene encoding the protease was amplified by PCR and fused with regulatory elements and homology regions for recombination into the *B. subtilis* genome.

The linear integration construct was a SOE-PCR fusion product (Horton, R. M., Hunt, H. D., Ho, S. N., Pullen, J. K. and Pease, L. R. (1989) *Engineering hybrid genes without the use of restriction enzymes, gene splicing by overlap extension Gene* 77: 61-68) made by fusion of the gene between two *Bacillus subtilis* chromosomal regions along with strong promoters and a chloramphenicol resistance marker. The SOE PCR method is also described in patent application WO 2003095658.

The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

The gene was expressed with a *Bacillus clausii* secretion signal (encoding the following amino acid sequence: MKKPLGKIVASTALLISVAFSSSIASA (SEQ ID NO: 5)) replacing the native secretion signal.

The SOE-PCR product was transformed into *Bacillus subtilis* and integrated in the chromosome by homologous recombination into the pectate lyase locus. Subsequently a recombinant *Bacillus subtilis* clone containing the integrated expression construct was grown in liquid culture. The culture broth was centrifuged (20000×g, 20 min) and the supernatant was carefully decanted from the precipitate and used for purification of the enzyme.

The supernatant was filtered through a Nalgene 0.2 μm filtration unit in order to remove the rest of the *Bacillus* host cells. The 0.2 μm filtrate was applied to a Bacitracin agarose column (from Upfront chromatography) equilibrated in 100 mM $H_3BO_3$, 10 mM MES, 2 mM $CaCl_2$, pH 6. After washing the column extensively with the equilibration buffer, the S8 protease was eluted with 100 mM $H_3BO_3$, 10 mM MES, 2 mM $CaCl_2$, 1 M NaCl, pH 6 with 25% (v/v) 2-propanol. The eluted peak was transferred to 100 mM $H_3BO_3$, 10 mM MES, 2 mM $CaCl_2$, pH 6 on a G25 sephadex column (from GE Healthcare). The G25 sephadex transferred S8 protease was used for further experiments.

When this purified product was analysed by SDS-PAGE only one major band was seen on the coomassie stained SDS-PAGE gel. Protease activity of the purified product was demonstrated using the Protazyme AK assay.

Example 8

Determination of Molecular Weight of the Jeotgalibacillus sp-13376 S8A Protease

Intact molecular weight analysis of the purified enzyme was performed using a MAXIS II electrospray mass spectrometer (Bruker Daltonik GmbH, Bremen, DE). The samples were diluted to 0.1 mg/ml in MQ water. The diluted sample was applied to an Aeris Widepore C4 column (Phenomenex). The sample was washed and eluted from the column running an acetonitrile linear gradient and introduced to the electrospray source with a flow of 300 ml/min by an Ultimate 3000 LC system (Dionex). Data analysis was performed with DataAnalysis version 4.2 (Bruker Daltonik GmbH, Bremen, DE). The molecular weight of the sample was calculated by Maximum Entropy deconvolution of the raw data in the range 10,000 to 40,000 Da. The dominant peak observed at molecular weight of 32136.77 Da corresponds within 0.03 Da to the calculated molecular weight of the mature protease in SEQ ID: 4.

Example 9

Wash Performance of the Jeotgalibacillus sp-13376 S8A Protease in Automatic Mechanical Stress Assay (AMSA)

In order to assess the wash performance in laundry, washing experiments were performed using the Automatic Mechanical Stress Assay (AMSA). The laundry experiments were conducted under the experimental conditions specified below:

TABLE 9

| AMSA experimental conditions: | |
|---|---|
| Test solution volume | 140 μL detergent per slot; 20 μL enzyme per slot |
| pH | As is |
| Wash time | 20 minutes |
| Temperature | 40° C. |
| Water hardness | 15°dH-$Ca^{2+}$/$Mg^{2+}$/$HCO_3^-$ 4:1:7.5 |
| Protease dosage | 0-7.5-15-30-60 nM |
| Test materials | PC-05 (Blood/milk/ink on cotton/polyester) |
| | PC-03 (Chocolate-milk/ink on cotton/polyester) |

The protease prepared in Examples 6 and 7 was tested in AMSA wash as described. The test was performed in different detergents on different stains at 40° C. Wash performance was compared with a well-known protease for detergent, Savinase (SEQ ID NO: 6), a protease derived from Bacillus lentus. The results are shown in table 10.

TABLE 10

Delta intensities of Jeotgalibacillus sp-13376 and Savinase relative to the liquid detergents without protease.

| | Jeotgalibacillus sp-13376 | | | | Savinase | | | |
|---|---|---|---|---|---|---|---|---|
| Condition | 7.5 nM | 15 nM | 30 nM | 60 nM | 7.5 nM | 15 nM | 30 nM | 60 nM |
| Det LF, 40° C., PC-05 | 30 | 45 | 52 | 58 | 41 | 49 | 54 | 56 |
| Det LF, 40° C., PC-03 | 20 | 26 | 34 | 41 | 19 | 24 | 29 | 33 |

The results show that the Jeotgalibacillus sp-13376 S8 protease shows significant wash performance in liquid detergents. Especially on cocoa the S8 protease from Jeotgalibacillus sp-13376 shows superior wash performance relative to Savinase.

The invention claimed is:

1. A nucleic acid construct or expression vector comprising a polynucleotide encoding a polypeptide having protease activity, wherein the polypeptide is operably linked to one or more heterologous control sequences that direct the production of the polypeptide in an expression host, and wherein the polypeptide is selected from the group consisting of:
   (a) a polypeptide having at least 90%, at least 91%, at least 92%, at least 93%, at least 94%, at least 95%, at least 95.5%, at least 96.5%, at least 97%, at least 97.5%, at least 98%, at least 98.5%, at least 99%, at least 99.5%, or 100% sequence identity to the mature polypeptide of SEQ ID NO: 2, or the mature polypeptide of SEQ ID NO: 4 and
   (b) a polypeptide encoded by a polynucleotide having at least 90%, at least 91%, at least 92%, at least 93%, at least 94%, at least 95%, at least 95.5%, at least 96.5%, at least 97%, at least 97.5%, at least 98%, at least 98.5%, at least 99%, at least 99.5%, or 100% sequence identity to the mature polypeptide coding sequence of SEQ ID NO: 1, or to the mature polypeptide coding sequence of SEQ ID NO: 3.

2. A recombinant host cell comprising a polynucleotide encoding a polypeptide having protease activity, wherein the polynucleotide is operably linked to one or more control sequences that direct the production of the polypeptide, wherein the polypeptide is selected from the group consisting of:
   (a) a polypeptide having at least 90%, at least 91%, at least 92%, at least 93%, at least 94%, at least 95%, at least 95.5%, at least 96.5%, at least 97%, at least 97.5%, at least 98%, at least 98.5%, at least 99%, at least 99.5%, or 100% sequence identity to the mature polypeptide of SEQ ID NO: 2, or the mature polypeptide of SEQ ID NO: 4 and
   (b) a polypeptide encoded by a polynucleotide having at least 90%, at least 91%, at least 92%, at least 93%, at least 94%, at least 95%, at least 95.5%, at least 96.5%, at least 97%, at least 97.5%, at least 98%, at least 98.5%, at least 99%, at least 99.5%, or 100% sequence identity to the mature polypeptide coding sequence of SEQ ID NO: 1, or to the mature polypeptide coding sequence of SEQ ID NO: 3.

3. A method of producing a polypeptide having protease activity comprising:
   (a) cultivating the host cell of claim 2 under conditions conducive for production of the polypeptide; and
   (b) recovering the polypeptide.

4. The method of claim 3, wherein the polypeptide has at least 95% sequence identity to the mature polypeptide of SEQ ID NO: 2, or the mature polypeptide of SEQ ID NO: 4.

5. The method of claim 3, wherein the polypeptide has at least 97% sequence identity to the mature polypeptide of SEQ ID NO: 2, or the mature polypeptide of SEQ ID NO: 4.

6. The method of claim 3, wherein the polypeptide has at least 99% sequence identity to the mature polypeptide of SEQ ID NO: 2, or the mature polypeptide of SEQ ID NO: 4.

7. The method of claim 3, wherein the polypeptide comprises the mature polypeptide of SEQ ID NO: 2, or the mature polypeptide of SEQ ID NO: 4.

8. The method of claim 3, wherein the polypeptide consists of the mature polypeptide of SEQ ID NO: 2, or the mature polypeptide of SEQ ID NO: 4.

9. A method of cleaning laundry or dishware, comprising contacting laundry or dishware with a detergent composition comprising a polypeptide having protease activity selected from the group consisting of:
   (a) a polypeptide having at least 90%, at least 91%, at least 92%, at least 93%, at least 94%, at least 95%, at least 95.5%, at least 96.5%, at least 97%, at least 97.5%, at least 98%, at least 98.5%, at least 99%, at least 99.5%, or 100% sequence identity to the mature polypeptide of SEQ ID NO: 2, or the mature polypeptide of SEQ ID NO: 4 and
   (b) a polypeptide encoded by a polynucleotide having at least 90%, at least 91%, at least 92%, at least 93%, at least 94%, at least 95%, at least 95.5%, at least 96.5%, at least 97%, at least 97.5%, at least 98%, at least 98.5%, at least 99%, at least 99.5%, or 100% sequence identity to the mature polypeptide coding sequence of SEQ ID NO: 1, or to the mature polypeptide coding sequence of SEQ ID NO: 3.

10. The method of claim 9, wherein the polypeptide has at least 95% sequence identity to the mature polypeptide of SEQ ID NO: 2, or the mature polypeptide of SEQ ID NO: 4.

11. The method of claim 9, wherein the polypeptide has at least 97% sequence identity to the mature polypeptide of SEQ ID NO: 2, or the mature polypeptide of SEQ ID NO: 4.

12. The method of claim 9, wherein the polypeptide has at least 99% sequence identity to the mature polypeptide of SEQ ID NO: 2, or the mature polypeptide of SEQ ID NO: 4.

13. The method of claim 9, wherein the polypeptide comprises the mature polypeptide of SEQ ID NO: 2, or the mature polypeptide of SEQ ID NO: 4.

14. The method of claim 9, wherein the polypeptide consists of the mature polypeptide of SEQ ID NO: 2, or the mature polypeptide of SEQ ID NO: 4.

* * * * *

SEQUENCE LISTING

```
<160> NUMBER OF SEQ ID NOS: 6

<210> SEQ ID NO 1
<211> LENGTH: 1284
<212> TYPE: DNA
<213> ORGANISM: Psychrobacillus psychrodurans
<220> FEATURE:
<221> NAME/KEY: sig_peptide
<222> LOCATION: (1)..(87)
<220> FEATURE:
<221> NAME/KEY: CDS
<222> LOCATION: (1)..(1281)
<220> FEATURE:
<221> NAME/KEY: misc_structure
<222> LOCATION: (88)..(342)
<223> OTHER INFORMATION: propeptide
<220> FEATURE:
<221> NAME/KEY: mat_peptide
```

<222> LOCATION: (343)..(1281)

<400> SEQUENCE: 1

| | | |
|---|---|---|
| atg aac aaa gca aaa tta tta tta cta agt gca gca tta atc ggt<br>Met Asn Lys Ala Lys Leu Leu Leu Leu Ser Ala Ala Leu Ile Gly<br>     -110              -105             -100 | 45 | |
| tca tta aca ata cca ctg caa ggt act tca tta gta aac gca act tct<br>Ser Leu Thr Ile Pro Leu Gln Gly Thr Ser Leu Val Asn Ala Thr Ser<br>           -95              -90              -85 | 93 | |
| tcc gaa tta att gat tct gct aaa gga tca gag aca ttt cga gtt tat<br>Ser Glu Leu Ile Asp Ser Ala Lys Gly Ser Glu Thr Phe Arg Val Tyr<br>       -80              -75              -70 | 141 | |
| gtt gaa agt aat aat aaa tct aca aaa aat aat ata aaa aat caa tac<br>Val Glu Ser Asn Asn Lys Ser Thr Lys Asn Asn Ile Lys Asn Gln Tyr<br>       -65              -60              -55 | 189 | |
| caa gtt cgt tgg gag tta act gag aat ggt ttc tcc act aat atg aac<br>Gln Val Arg Trp Glu Leu Thr Glu Asn Gly Phe Ser Thr Asn Met Asn<br>       -50              -45              -40 | 237 | |
| caa aac caa tat gat gca ctt caa aaa aac aaa aat ata acc gta aca<br>Gln Asn Gln Tyr Asp Ala Leu Gln Lys Asn Lys Asn Ile Thr Val Thr<br>-35              -30              -25              -20 | 285 | |
| aaa atg gac aaa gta aca ctt gat gta gat gta cgt tct tct gaa ttc<br>Lys Met Asp Lys Val Thr Leu Asp Val Asp Val Arg Ser Ser Glu Phe<br>               -15              -10              -5 | 333 | |
| gaa aca atg gca ggt gaa tat cca acc gag caa acc cct tgg gga ata<br>Glu Thr Met Ala Gly Glu Tyr Pro Thr Glu Gln Thr Pro Trp Gly Ile<br>       -1   1               5               10 | 381 | |
| aaa gct att tat aat aat tca agt tta acg gcc act tct ggt gga gca<br>Lys Ala Ile Tyr Asn Asn Ser Ser Leu Thr Ala Thr Ser Gly Gly Ala<br>       15              20              25 | 429 | |
| ggt att aat att gcg gtt tta gat act gga gta aat att aat cat tat<br>Gly Ile Asn Ile Ala Val Leu Asp Thr Gly Val Asn Ile Asn His Tyr<br>30              35              40              45 | 477 | |
| gac tta act aat aca gtg gaa caa tgt aaa aac ttc act acc gct act<br>Asp Leu Thr Asn Thr Val Glu Gln Cys Lys Asn Phe Thr Thr Ala Thr<br>               50              55              60 | 525 | |
| cca att gtc aat aat agc tgt aat gat gca aat gga cat ggt acg cat<br>Pro Ile Val Asn Asn Ser Cys Asn Asp Ala Asn Gly His Gly Thr His<br>               65              70              75 | 573 | |
| gtt gcc ggc act gcc ctt gca gat ggt ggg agt gat gga gca gga att<br>Val Ala Gly Thr Ala Leu Ala Asp Gly Gly Ser Asp Gly Ala Gly Ile<br>       80              85              90 | 621 | |
| tac gga gta gca cca agt gct gac tta tgg gct tat aaa gtt cta gga<br>Tyr Gly Val Ala Pro Ser Ala Asp Leu Trp Ala Tyr Lys Val Leu Gly<br>       95              100             105 | 669 | |
| gat gat gga tcg gga tat tca gat gat atc gcc gca gca att aga cat<br>Asp Asp Gly Ser Gly Tyr Ser Asp Asp Ile Ala Ala Ala Ile Arg His<br>110             115             120             125 | 717 | |
| gca gcc gac caa gcc gtt tct acg gga act aaa aca gtt att aat atg<br>Ala Ala Asp Gln Ala Val Ser Thr Gly Thr Lys Thr Val Ile Asn Met<br>               130             135             140 | 765 | |
| tcc ctt ggc tct tct gct agt aat agt tta ata aca agt gct gtg aat<br>Ser Leu Gly Ser Ser Ala Ser Asn Ser Leu Ile Thr Ser Ala Val Asn<br>               145             150             155 | 813 | |
| tac gct tat aac aaa gga gta tta ata att gca gct gca gga aat tca<br>Tyr Ala Tyr Asn Lys Gly Val Leu Ile Ile Ala Ala Ala Gly Asn Ser<br>               160             165             170 | 861 | |
| ggt cct tcc caa gga tca ata ggt tat cca gga gcc tta gta aat gct<br>Gly Pro Ser Gln Gly Ser Ile Gly Tyr Pro Gly Ala Leu Val Asn Ala<br>       175             180             185 | 909 | |

```
gtg gct gta gca gct cta gaa aat cgt caa caa aac ggt aca tac cgg      957
Val Ala Val Ala Ala Leu Glu Asn Arg Gln Gln Asn Gly Thr Tyr Arg
190             195                 200                 205 gtt gct gat ttc tcc tca cgc gga tat agc tcc act gac gga gac tat     1005
Val Ala Asp Phe Ser Ser Arg Gly Tyr Ser Ser Thr Asp Gly Asp Tyr
        210                 215                 220 gta att caa caa gga gat ata gaa att tca gct cct gga gca tct ata     1053
Val Ile Gln Gln Gly Asp Ile Glu Ile Ser Ala Pro Gly Ala Ser Ile
225                 230                 235 tat tcc act tgg aat aat ggt gga tat aat aca ata agc gga aca tca     1101
Tyr Ser Thr Trp Asn Asn Gly Gly Tyr Asn Thr Ile Ser Gly Thr Ser
        240                 245                 250 atg gcc act ccc cat gta gct gga ctg gca gca aag gta tgg tcc caa     1149
Met Ala Thr Pro His Val Ala Gly Leu Ala Ala Lys Val Trp Ser Gln
255                 260                 265 aac ccc tct tgg tcc cat aca caa ctc cgc aca aat tta caa acc cgt     1197
Asn Pro Ser Trp Ser His Thr Gln Leu Arg Thr Asn Leu Gln Thr Arg
270                 275                 280                 285 gcg aga gca gta gat att aaa gga ggt agc ggc gca gca act ggc gac     1245
Ala Arg Ala Val Asp Ile Lys Gly Gly Ser Gly Ala Ala Thr Gly Asp
            290                 295                 300 gac tat gct tct ggt ttc ggt ttt gca aga gtg caa taa                 1284
Asp Tyr Ala Ser Gly Phe Gly Phe Ala Arg Val Gln
            305                 310
```

<210> SEQ ID NO 2
<211> LENGTH: 427
<212> TYPE: PRT
<213> ORGANISM: Psychrobacillus psychrodurans

<400> SEQUENCE: 2

Met Asn Lys Ala Lys  Leu Leu Leu Leu Ser  Ala Ala Leu Ile Gly
                -110                -105                -100

Ser Leu Thr Ile Pro Leu Gln Gly Thr Ser Leu Val Asn Ala Thr Ser
                -95                 -90                 -85

Ser Glu Leu Ile Asp Ser Ala Lys Gly Ser Glu Thr Phe Arg Val Tyr
            -80                 -75                 -70

Val Glu Ser Asn Asn Lys Ser Thr Lys Asn Asn Ile Lys Asn Gln Tyr
        -65                 -60                 -55

Gln Val Arg Trp Glu Leu Thr Glu Asn Gly Phe Ser Thr Asn Met Asn
    -50                 -45                 -40

Gln Asn Gln Tyr Asp Ala Leu Gln Lys Asn Lys Asn Ile Thr Val Thr
-35                 -30                 -25                 -20

Lys Met Asp Lys Val Thr Leu Asp Val Asp Val Arg Ser Ser Glu Phe
                -15                 -10                 -5

Glu Thr Met Ala Gly Glu Tyr Pro Thr Glu Gln Thr Pro Trp Gly Ile
        -1  1                 5                  10

Lys Ala Ile Tyr Asn Asn Ser Ser Leu Thr Ala Thr Ser Gly Gly Ala
            15                  20                  25

Gly Ile Asn Ile Ala Val Leu Asp Thr Gly Val Asn Ile Asn His Tyr
30                  35                  40                  45

Asp Leu Thr Asn Thr Val Glu Gln Cys Lys Asn Phe Thr Ala Thr
                50                  55                  60

Pro Ile Val Asn Asn Ser Cys Asn Asp Ala Asn Gly His Gly Thr His
            65                  70                  75

Val Ala Gly Thr Ala Leu Ala Asp Gly Gly Ser Asp Gly Ala Gly Ile
        80                  85                  90

```
Tyr Gly Val Ala Pro Ser Ala Asp Leu Trp Ala Tyr Lys Val Leu Gly
     95                 100                 105

Asp Asp Gly Ser Gly Tyr Ser Asp Ile Ala Ala Ile Arg His
110                 115                 120                 125

Ala Ala Asp Gln Ala Val Ser Thr Gly Thr Lys Thr Val Ile Asn Met
             130                 135                 140

Ser Leu Gly Ser Ser Ala Ser Asn Ser Leu Ile Thr Ser Ala Val Asn
             145                 150                 155

Tyr Ala Tyr Asn Lys Gly Val Leu Ile Ile Ala Ala Gly Asn Ser
             160                 165                 170

Gly Pro Ser Gln Gly Ser Ile Gly Tyr Pro Gly Ala Leu Val Asn Ala
     175                 180                 185

Val Ala Val Ala Ala Leu Glu Asn Arg Gln Gln Asn Gly Thr Tyr Arg
190                 195                 200                 205

Val Ala Asp Phe Ser Ser Arg Gly Tyr Ser Ser Thr Asp Gly Asp Tyr
             210                 215                 220

Val Ile Gln Gln Gly Asp Ile Glu Ile Ser Ala Pro Gly Ala Ser Ile
             225                 230                 235

Tyr Ser Thr Trp Asn Asn Gly Tyr Asn Thr Ile Ser Gly Thr Ser
     240                 245                 250

Met Ala Thr Pro His Val Ala Gly Leu Ala Ala Lys Val Trp Ser Gln
255                 260                 265

Asn Pro Ser Trp Ser His Thr Gln Leu Arg Thr Asn Leu Gln Thr Arg
270                 275                 280                 285

Ala Arg Ala Val Asp Ile Lys Gly Gly Ser Gly Ala Thr Gly Asp
             290                 295                 300

Asp Tyr Ala Ser Gly Phe Gly Phe Ala Arg Val Gln
             305                 310
```

<210> SEQ ID NO 3
<211> LENGTH: 1263
<212> TYPE: DNA
<213> ORGANISM: Jeotgalibacillus sp.
<220> FEATURE:
<221> NAME/KEY: misc_feature
<222> LOCATION: (1)..(3)
<223> OTHER INFORMATION: The first amino acid in the polypeptide shown
      in SEQ ID NO: 2 and encoded by the polynucleotide shown in SEQ ID
      NO:1 should be Met, not Leu. When the first codon is ttg a Met is
      inserted though ttg normally codes for Leu
<220> FEATURE:
<221> NAME/KEY: sig_peptide
<222> LOCATION: (1)..(78)
<220> FEATURE:
<221> NAME/KEY: CDS
<222> LOCATION: (1)..(1260)
<220> FEATURE:
<221> NAME/KEY: misc_structure
<222> LOCATION: (79)..(321)
<223> OTHER INFORMATION: pro_peptide
<220> FEATURE:
<221> NAME/KEY: mat_peptide
<222> LOCATION: (322)..(1260)

<400> SEQUENCE: 3

```
ttg aaa aag tca aag aaa att ttt atg agt ctc ttg tta act gcc agt        48
Leu Lys Lys Ser Lys Lys Ile Phe Met Ser Leu Leu Leu Thr Ala Ser
        -105                -100                 -95 cta gca atg cct gct atg tct gcg gga gct aac tca gac aca ctg aac        96
Leu Ala Met Pro Ala Met Ser Ala Gly Ala Asn Ser Asp Thr Leu Asn
    -90                 -85                 -80
```

```
aag gca gag aaa ttt cgt gtg ttt gta gaa acg acg aac agt gtt tca      144
Lys Ala Glu Lys Phe Arg Val Phe Val Glu Thr Thr Asn Ser Val Ser
-75             -70             -65             -60 acg gct tcc gtt aaa aag cag cat gac gta cgc tgg cag tta act gca      192
Thr Ala Ser Val Lys Lys Gln His Asp Val Arg Trp Gln Leu Thr Ala
            -55             -50             -45 aac gga ttt tcc acc gaa atg aat gag att caa ttc aaa gcg ttg cag      240
Asn Gly Phe Ser Thr Glu Met Asn Glu Ile Gln Phe Lys Ala Leu Gln
        -40             -35             -30 aaa aat caa aat gtc aat gtg aca aaa gtg caa gaa gtt acg ctt gat      288
Lys Asn Gln Asn Val Asn Val Thr Lys Val Gln Glu Val Thr Leu Asp
    -25             -20             -15 acg gat gtt cgg gct ttg caa aac gag gtg ctg gca gca gaa tat ccc      336
Thr Asp Val Arg Ala Leu Gln Asn Glu Val Leu Ala Ala Glu Tyr Pro
-10              -5              -1   1              5 act cac caa acg cct tgg gga atc aaa gcg atc tac aat aat cca aat      384
Thr His Gln Thr Pro Trp Gly Ile Lys Ala Ile Tyr Asn Asn Pro Asn
            10              15              20 caa acc aca aca tca ggc gga cag gga atc aat att gcg gtc ctt gat      432
Gln Thr Thr Thr Ser Gly Gly Gln Gly Ile Asn Ile Ala Val Leu Asp
        25              30              35 acg ggt gta aat gtt aat cac tat gat ttg gtg aac acg gtg gag caa      480
Thr Gly Val Asn Val Asn His Tyr Asp Leu Val Asn Thr Val Glu Gln
    40              45              50 tgc aaa gat ttc act caa tcc aac ccg cta gtg aac ggc tca tgt aat      528
Cys Lys Asp Phe Thr Gln Ser Asn Pro Leu Val Asn Gly Ser Cys Asn
55              60              65 gat gca aat gga cat ggt act cac gta gcc ggc tct gcc ctg gct gac      576
Asp Ala Asn Gly His Gly Thr His Val Ala Gly Ser Ala Leu Ala Asp
70              75              80              85 ggc gga agt gat aaa gcc ggg atc tac ggt gtg gca ccg gat tca gat      624
Gly Gly Ser Asp Lys Ala Gly Ile Tyr Gly Val Ala Pro Asp Ser Asp
            90              95              100 ctt tgg gct tac aaa gtg tta ggt gac aat ggt tct ggt tat tct gat      672
Leu Trp Ala Tyr Lys Val Leu Gly Asp Asn Gly Ser Gly Tyr Ser Asp
        105             110             115 gat att gcg gct gcg atc cgt cat gca gca gat caa gca gta agt aca      720
Asp Ile Ala Ala Ala Ile Arg His Ala Ala Asp Gln Ala Val Ser Thr
    120             125             130 ggc act aaa aca gtt atc aac atg tct ctc ggt tct gca gtt aat gac      768
Gly Thr Lys Thr Val Ile Asn Met Ser Leu Gly Ser Ala Val Asn Asp
135             140             145 tcc ttg atc tca agc gca gta aac tat gcc tac tcc aga ggc gtc ctg      816
Ser Leu Ile Ser Ser Ala Val Asn Tyr Ala Tyr Ser Arg Gly Val Leu
150             155             160             165 att gtg gca gca gcg ggt aac tca ggg cct aat caa ggc aca atc ggt      864
Ile Val Ala Ala Ala Gly Asn Ser Gly Pro Asn Gln Gly Thr Ile Gly
            170             175             180 tat cct ggt gcc ctg cca aat gct att gct gtt gca gct ctt gaa aat      912
Tyr Pro Gly Ala Leu Pro Asn Ala Ile Ala Val Ala Ala Leu Glu Asn
        185             190             195 cag caa caa aac ggc acc tac cgt gta gct gac ttt tca tct cgc ggc      960
Gln Gln Gln Asn Gly Thr Tyr Arg Val Ala Asp Phe Ser Ser Arg Gly
    200             205             210 ttt gca gca act gcc gga gac tat atc atc cag caa ggg gat att gaa      1008
Phe Ala Ala Thr Ala Gly Asp Tyr Ile Ile Gln Gln Gly Asp Ile Glu
215             220             225 atc tct gct cca ggt gcg gcg atc tac tct act tgg cat aac ggc gga      1056
Ile Ser Ala Pro Gly Ala Ala Ile Tyr Ser Thr Trp His Asn Gly Gly
230             235             240             245
```

```
tac aac aca atc agc ggt act tcc atg gca acg cca cac gta gca gga      1104
Tyr Asn Thr Ile Ser Gly Thr Ser Met Ala Thr Pro His Val Ala Gly
                250                 255                 260 ctt gcg gct aaa gta tgg gcc caa aac cca agc tgg tca cac act cag      1152
Leu Ala Ala Lys Val Trp Ala Gln Asn Pro Ser Trp Ser His Thr Gln
                265                 270                 275 ctt aga aca aac ctt caa aac cgg gca aaa gcc gtt gac att aaa ggc      1200
Leu Arg Thr Asn Leu Gln Asn Arg Ala Lys Ala Val Asp Ile Lys Gly
                280                 285                 290 gga ctc gga gct gca aca ggc gac gac tac gct tca gga ttt gga ttt      1248
Gly Leu Gly Ala Ala Thr Gly Asp Asp Tyr Ala Ser Gly Phe Gly Phe
                295                 300                 305 gcg cga gtg aat taa                                                   1263
Ala Arg Val Asn
310

<210> SEQ ID NO 4
<211> LENGTH: 420
<212> TYPE: PRT
<213> ORGANISM: Jeotgalibacillus sp.

<400> SEQUENCE: 4

Leu Lys Lys  Ser Lys Lys Ile Phe  Met Ser Leu Leu Leu Thr Ala Ser
        -105                -100                 -95

Leu Ala Met Pro Ala Met Ser Ala Gly Ala Asn Ser Asp Thr Leu Asn
         -90             -85                 -80

Lys Ala Glu Lys Phe Arg Val Phe Val Glu Thr Thr Asn Ser Val Ser
-75                  -70                 -65                 -60

Thr Ala Ser Val Lys Lys Gln His Asp Val Arg Trp Gln Leu Thr Ala
                 -55                 -50                 -45

Asn Gly Phe Ser Thr Glu Met Asn Glu Ile Gln Phe Lys Ala Leu Gln
             -40                 -35                 -30

Lys Asn Gln Asn Val Asn Val Thr Lys Val Gln Glu Val Thr Leu Asp
         -25                 -20                 -15

Thr Asp Val Arg Ala Leu Gln Asn Glu Val Leu Ala Ala Glu Tyr Pro
 -10                  -5                  -1   1                  5

Thr His Gln Thr Pro Trp Gly Ile Lys Ala Ile Tyr Asn Asn Pro Asn
                 10                  15                  20

Gln Thr Thr Thr Ser Gly Gly Gln Gly Ile Asn Ile Ala Val Leu Asp
                 25                  30                  35

Thr Gly Val Asn Val Asn His Tyr Asp Leu Val Asn Thr Val Glu Gln
             40                  45                  50

Cys Lys Asp Phe Thr Gln Ser Asn Pro Leu Val Asn Gly Ser Cys Asn
 55                  60                  65

Asp Ala Asn Gly His Gly Thr His Val Ala Gly Ser Ala Leu Ala Asp
 70                  75                  80                  85

Gly Gly Ser Asp Lys Ala Gly Ile Tyr Gly Val Ala Pro Asp Ser Asp
                 90                  95                 100

Leu Trp Ala Tyr Lys Val Leu Gly Asp Asn Gly Ser Gly Tyr Ser Asp
             105                 110                 115

Asp Ile Ala Ala Ala Ile Arg His Ala Ala Asp Gln Ala Val Ser Thr
             120                 125                 130

Gly Thr Lys Thr Val Ile Asn Met Ser Leu Gly Ser Ala Val Asn Asp
         135                 140                 145

Ser Leu Ile Ser Ser Ala Val Asn Tyr Ala Tyr Ser Arg Gly Val Leu
150                 155                 160                 165
```

```
Ile Val Ala Ala Ala Gly Asn Ser Gly Pro Asn Gln Gly Thr Ile Gly
                170                 175                 180

Tyr Pro Gly Ala Leu Pro Asn Ala Ile Ala Val Ala Ala Leu Glu Asn
            185                 190                 195

Gln Gln Gln Asn Gly Thr Tyr Arg Val Ala Asp Phe Ser Ser Arg Gly
        200                 205                 210

Phe Ala Ala Thr Ala Gly Asp Tyr Ile Ile Gln Gln Gly Asp Ile Glu
    215                 220                 225

Ile Ser Ala Pro Gly Ala Ala Ile Tyr Ser Thr Trp His Asn Gly Gly
230                 235                 240                 245

Tyr Asn Thr Ile Ser Gly Thr Ser Met Ala Thr Pro His Val Ala Gly
                250                 255                 260

Leu Ala Ala Lys Val Trp Ala Gln Asn Pro Ser Trp Ser His Thr Gln
            265                 270                 275

Leu Arg Thr Asn Leu Gln Asn Arg Ala Lys Ala Val Asp Ile Lys Gly
        280                 285                 290

Gly Leu Gly Ala Ala Thr Gly Asp Asp Tyr Ala Ser Gly Phe Gly Phe
    295                 300                 305

Ala Arg Val Asn
310

<210> SEQ ID NO 5
<211> LENGTH: 27
<212> TYPE: PRT
<213> ORGANISM: Bacillus clausii

<400> SEQUENCE: 5

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 6
<211> LENGTH: 269
<212> TYPE: PRT
<213> ORGANISM: Bacillus lentus

<400> SEQUENCE: 6

Ala Gln Ser Val Pro Trp Gly Ile Arg Arg Val Gln Ala Pro Thr Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Glu Asn Gly His Gly Thr
    50                  55                  60

His Ala Ala Gly Thr Ile Ala Ala Leu Asp Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140
```

```
Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asp Gly Thr Ser Met Ala Thr Pro His Val Ala Gly Ala
    210                 215                 220

Ala Ala Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```